United States Patent
Ogilvie et al.

(10) Patent No.: US 6,699,292 B2
(45) Date of Patent: Mar. 2, 2004

(54) INTERPHALANGEAL JOINT REPLACEMENT

(75) Inventors: William F. Ogilvie, Austin, TX (US); Charles W. Mumme, Austin, TX (US); John K. Stanley, Lancashire (GB)

(73) Assignee: Ascension Orthopedics, Inc., Austin, TX (US)

( * ) Notice: Subject to any disclaimer, the term of this patent is extended or adjusted under 35 U.S.C. 154(b) by 0 days.

(21) Appl. No.: 09/995,365

(22) Filed: Nov. 27, 2001

(65) Prior Publication Data

US 2002/0065561 A1 May 30, 2002

Related U.S. Application Data

(60) Provisional application No. 60/253,517, filed on Nov. 28, 2000.

(51) Int. Cl.$^7$ ................................................. A61F 2/42
(52) U.S. Cl. ................................................. 623/21.15
(58) Field of Search ........................... 623/16.11, 21.11, 623/21.12, 21.13, 21.14, 21.15, 21.16, 21.17, 21.18, 21.19, 20.27, 20.14, 20.15; 606/87

(56) References Cited

U.S. PATENT DOCUMENTS

| | | | |
|---|---|---|---|
| 3,991,425 A | 11/1976 | Martin et al. | |
| 4,231,121 A | 11/1980 | Lewis | |
| 4,242,759 A | * 1/1981 | White | 623/21.15 |
| 4,725,280 A | 2/1988 | Laure | |
| 5,092,896 A | 3/1992 | Meuli et al. | |
| 5,405,400 A | 4/1995 | Linscheid et al. | |
| 5,405,401 A | 4/1995 | Lippincott, III et al. | |
| 5,458,647 A | 10/1995 | Brochier et al. | |
| 5,458,648 A | * 10/1995 | Berman et al. | 623/21.19 |
| 5,645,605 A | 7/1997 | Klawitter | |
| 5,725,585 A | * 3/1998 | Zobel | 623/21.19 |
| 5,728,163 A | * 3/1998 | Maksene | 623/21.15 |
| 5,782,927 A | 7/1998 | Klawitter et al. | |
| 5,938,700 A | * 8/1999 | Lippincott, III | 623/21.15 |
| 6,053,945 A | 4/2000 | O'Neil et al. | |
| 6,506,215 B1 | * 1/2003 | Letot et al. | 623/20.29 |

FOREIGN PATENT DOCUMENTS

| | | |
|---|---|---|
| DE | 196 51 546 A | 6/1997 |
| GB | 2308068 A | 6/1997 |

OTHER PUBLICATIONS

Linscheid, MD, et al., *Development of a Surface Replacement Arthroplasty for Proximal Interphalangeal Joints*, The Journal of Hand Surgery, 1997, 22A:, No. 2, pp. 286–298.
Linscheid, MD, et al., *Proximal Interphalangeal Joint Arthroplasty With a Total Joint Design*, Mayo Clin. Proc., Apr. 1979, Vo. 54, pp. 227–240.

* cited by examiner

*Primary Examiner*—Pedro Philogene
(74) *Attorney, Agent, or Firm*—Fitch, Even, Tabin & Flannery (57) ABSTRACT

First and second elements that have mating heads form an interphalangeal joint prosthesis that allows smooth articulation dorsal to volar. The first element head has a proximal surface defined by two intersecting planes, a stem portion that extends longitudinally therefrom and a convex bicondylar articulating surface having a central valley. The second element has a biconcave articulating proximal surface which mates with the first element articulating surface and a stem portion that extends longitudinally from the distal surface thereof, with a notch being formed in a dorsal surface of the head at a location that does not disturb attachments to the dorsal tubercle or the function of the median band of the extensor expansion. Sets of such joint prostheses of varying sizes are provided which are designed so that adjacent sizes interfit. A method for treating a deteriorated PIP joint is described.

16 Claims, 10 Drawing Sheets

INTERPHALANGEAL JOINT REPLACEMENT

This application claims priority from U.S. Provisional Application Ser. No. 60/253,517, filed Nov. 28, 2000, the disclosure of which is expressly incorporated herein by reference.

This invention relates to a prosthetic joint adapted to replace a human joint and, more specifically, to an improved prosthetic joint adapted to replace an interphalangeal joint of the human finger.

BACKGROUND OF THE INVENTION

The first elongated bone (metacarpal) at the base of each finger is connected to a proximal phalangeal bone through the metacarpal-phalangeal (MCP) joint. The proximal phalangeal bone is connected to the middle phalangeal bone through the proximal interphalangeal (PIP) joint. The PIP joint can be flexed independently of the MCP or the distal interphalangeal (DIP) joint. This variable reciprocal motion, along with the opposability of the thumb, allows for grasping of objects and the performance of daily functions which are of critical importance to humans. Damage to the PIP joint through physical injury or disease can therefore be a severe physiological burden to inflicted humans.

Degenerative joint diseases: osteoarthritis (OA), post-traumatic arthritis, and rheumatoid arthritis (RA) of the PIP joint cause interminable pain and poor function of the finger. Patients who have mild symptoms often respond to rest, immobilization, nonsteroidal anti-inflammatory drugs or intra-articular injections of steroids. However, patients who have more severe forms of arthritis may require total joint replacement of the PIP joint.

The most common deformity in patients suffering from OA is narrowing of the articular cartilage of the PIP joint. OA is a hypertropic arthritis that results in degeneration of the articular cartilage which is often either primary or secondary to trauma or other conditions, and such degeneration of the cartilage causes movement of the joint to be painful. The usual solution is fusion of the joint which eliminates pain but renders the joint nonfunctional. This is particularly true in young patients with normal grip strength. The preferred solution is the installation of a prosthetic PIP joint, however, there has long been a need for a replacement joint which resurfaces the native joint, allows for normal joint motion, and withstands the joint reaction forces produced in patients with normal grip strength.

Various prosthetic joints have been developed to replace finger joints; however, most of these have involved the replacement of the MCP joint where the finger joins the hand. These prosthetic joints have typically involved some type of captive ball-and-socket arrangement for permitting a substantial range of pivoting movement in a vertical plane, while sometimes also permitting limited sideward displacement in an attempt to provide for motion which more closely correlates with the natural joint. Joints of this type are normally not suitable for replacing the proximal or distal interphalangeal joints of the finger because they typically possess a structure which is undesirably large and complex, i.e. interphalangeal joints desirably do not incorporate a capability for sideward or lateral pivoting.

Examples of finger joints which are designed specifically for replacing the human MCP joint are disclosed in U.S. Pat. Nos. 5,782,927, 4,731,087 and 4,231,121, with this latter patented joint being represented as also being suitable for use as a PIP or DIP joint. U.S. Pat. No. 4,725,280 discloses a joint which is designed specifically for use in replacing the human PIP joint or the DIP joint. More recent U.S. Pat. No. 5,728,163 (Mar. 17, 1998) discloses a MCP joint prosthesis which is alleged to also be useful as an interphalangeal joint prosthesis. Work was also done at The Mayo Clinic in the 1970's directed to the PIP joint, and this work is reported in an article by Linscheid, R. L. et al, entitled "Proximal Interphalangeal Joints Arthroplasty with a Total Joint Design", *Mayo Clin. Proc.*, 54, 227–240 (1979). Continuing work on this project was more recently reported in a further article by Linscheid et al. entitled "Development of a Surface Replacement Arthroplasty for Proximal Interphalangeal Joints", *The Journal of Hand Surgery*, 22a, 286–298 (1997).

Although various of these PIP joints have had limited success, they have not gained wide acceptance throughout the medical profession. Accordingly, the search has continued for improved joints particularly suited for the replacement of the PIP joint that are implantable in such a manner as to facilitate its attachment to the phalanges while at the same time providing a vertical range of pivoting movement which closely approximates natural joint movement.

One important design consideration for PIP prosthetic joints is minimizing the wear between the mating articular surfaces. Mating surfaces may conform to such an extent that biological fluids, which would normally provide joint lubrication, are expressed from the PIP prosthetic joint, and the resulting "dry joint" may experience increased friction between the congruent articulating surfaces. Thus, it is now felt that a prosthetic PIP joint should preferably avoid the use of substantially congruent articular surfaces.

Still another important design consideration for prosthetic PIP joints is preserving the structure and function of the ligamentous tissues which surround the joint. The collateral ligaments which run along each lateral side of the PIP joint comprise both fan-like collateral ligaments and cord-like collateral ligaments (see FIGS. 2*a* and 2*b*). The fan-like collateral ligaments insert at both sides of the distal portion of the proximal phalanx and serve to support the volar plate, thereby forming an important part of the overall PIP joint. The cord-like collateral ligaments, which also insert at both sides of the distal portion of the proximal phalanx, serve to resist subluxation-dislocation of the middle phalangeal bone; because they insert at about the center of rotation of the PIP joint, they do not undergo any dramatic change in tension during flexion/extension of the PIP joint. A prosthetic PIP joint should be designed so as to preferably not require the excision of the attachment sites or disruption of the collateral ligaments and/or the volar or palmar plate. Additionally, a prosthetic PIP joint should preferably not alter the manner in which the collateral ligaments and/or the volar plate wrap around the joint during PIP joint flexion and extension.

Figure 2C:
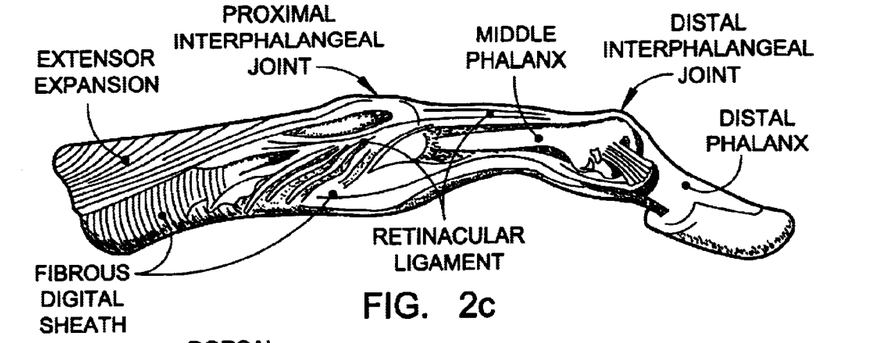
FIGS. 2c and d are side elevation views particularly illustrating the arrangement of the retinacular ligament of the normal PIP joint when the proximal phalangeal bone and the middle phalangeal bone are either in full extension or in full flexion.
Figure 2D:
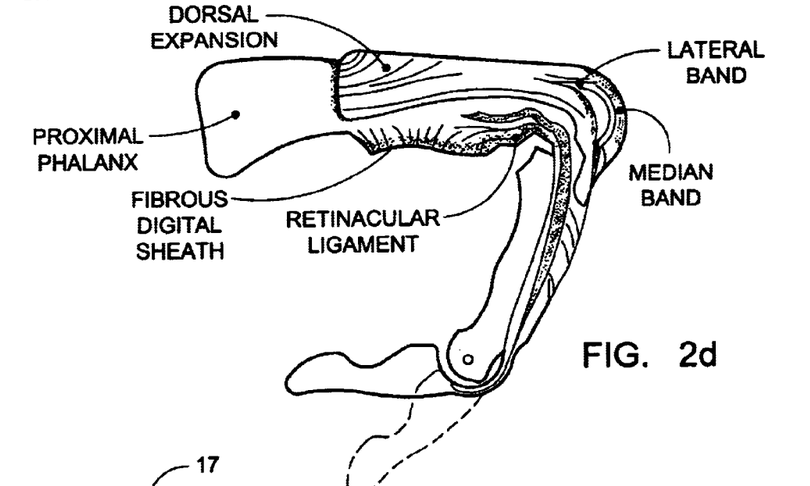

The retinacular ligaments cross each lateral side of the PIP joint as seen in FIGS. 2*c* and 2*d*. On flexing the DIP joint, each retinacular ligament becomes taut and pulls the PIP joint into flexion. Similarly, on extending the proximal joint, the distal joint is pulled by the retinacular ligament into nearly complete extension. A prosthetic joint should preferably not interfere with the function of the retinacular ligaments.

Yet another important design consideration for a prosthetic PIP joint is the preservation of the structure and function of the tendinous tissues which surround and motivate the PIP joint. The PIP joint can only flex and extend for it has just one degree of freedom. The extensor expansion is the extensor mechanism of the finger. The tendons of extensor digitorum form the extensor expansions of all fingers, see FIGS. 2a and 2b. The extensor digiti minimi tendon contributes to the extensor expansion of the little finger. The extensor indicis tendon contributes to the extensor expansion of the index finger. The lumbricals and interossei also contribute to the extensor expansions of the fingers. The tendons of flexor digitorum profundus (FDP) and flexsor digitorum superficialis (FDS) form the flexor mechanism of a finger. The FDS tendon crosses the bottom of the PIP joint and attaches to the proximal volar region of the middle phalanx. The FDP tendon crosses the bottoms of both the PIP and DIP joints to attach to proximal volar surface of the distal phalanx.

For any finger, the median band, also referred to as the "central slip", of the extensor expansion crosses the top of the PIP joint and attaches to the proximal dorsal surface of the middle phalanx. The median band of the extensor expansion wraps around the distal head of the proximal phalanx as the PIP joint is flexed from full extension to full flexion which, for the PIP joint, is approximately 100 degrees. The distal head of the proximal phalanx is bicondylar, as is the distal head of the middle phalanx, and the median band tracks between the condyles of the distal head in an intercondylar notch. The volar surface of the distal portion of the median band has a distinct region which mates with the intercondylar notch of the distal head of the proximal phalanx and which Professor John Stanley has recently named the Intercondylar Centering Pad (ICP). The ICP essentially fills the intercondylar notch, centering the median band of the extensor expansion between the condyles of the distal head of the proximal phalanx. The ICP enhances the lateral stability of the median band of extensor expansion as it wraps around the PIP joint during flexion/extension. If the median band were to slide laterally during extension of the PIP joint, the moment arm of the median band, i.e. the distance the tendon is from the center of rotation of the joint, would shorten which in turn would decrease the amount of extension torque applied to the PIP joint. Such a situation would likely result in an extension lag, i.e. an inability to fully extend the PIP joint.

The median band of the extensor expansion is taut during flexion of the PIP joint (see FIG. 2d) because of the passive elastic properties of the extensor muscles. If the median band were to slide laterally during flexion of the PIP joint, the volar subluxation/dislocation force created by the pull of the FDS and FDP tendons would only be resisted by the collateral ligaments and the articular surfaces of the PIP joint. Such a situation would increase the likelihood of volar subluxation-dislocation of the middle phalanx. A prosthetic PIP joint should preferably not alter the manner in which the median band and ICP of the extensor expansion wrap around the PIP joint during PIP joint flexion and extension.

The lateral bands of the extensor expansion cross each lateral side of the PIP joint, passing distally and wrapping dorsally to unite along the dorsal surface of the middle phalanx. The united lateral bands the cross the top of the DIP joint and attach to the proximal dorsal surface of the distal phalanx. During flexion of the PIP joint, the lateral bands (as they cross each lateral side of the PIP joint) slide from positions above the center of rotation of the PIP joint to positions below the center of rotation of the PIP joint. Proper prosthetic PIP joint design should have concern for the function of the lateral bands of the extensor expansion and allow the lateral bands to move normally during flexion-extension.

SUMMARY OF THE INVENTION

An implant device is provided for replacement of the complete PIP joint of the human finger in the form of a prosthesis composed of two complementary elements or members. One element, referred to as the PP (proximal phalangeal) element, replaces the distal articular portion of the proximal phalangeal bone, and the other element, referred to as the MP (middle phalangeal) element, replaces the proximal articular portion of the middle phalangeal bone. The PP element terminates in a generally bycondylar convex surface that articulates with a complementary biconcave surface formed at the proximal end of the MP element. By "biconcave" surface is meant a surface that has two side-by-side shallow smooth cavities having a curvature that is complementary to but not congruent with the convex surfaces of the two condyles. The implant device is provided in a limited range of sizes of PP elements and MP elements. To accommodate the expected variation in patient anatomy, design and dimensioning are carefully controlled so that the biconcave articular surface of a given size of a MP element will smoothly receive and mate with the convex articular condylar surfaces of the PP elements of at least two, but usually three, different sizes thereof, and vice versa. Also provided is an improved method for replacing a deteriorated interphalangeal joint.

The PP element's articular head has distal or a front bicondylar convex articular surface and a proximal or rear surface which will abut the bone in the form of two intersecting planes that extend to the dorsal and volar boundaries of the bicondylar convex articular surface. The convex bicondylar distal articular head of the PP element member has lateral planar sides which are parallel to the longitudinal axis thereof, but are sloped so that the width (longitudinally) of the dorsal region of the head is less than the width of the volar region of the head. These sloped planar lateral sides of the proximal head provide substantially free paths for the fan-like and cord-like collateral ligaments, the lateral bands of the extensor expanson and the retinacular ligaments which run along each lateral side of the of the PIP joint. The two planes that define the proximal surface of the PP element intersect along a line that lies volar of the longitudinal axis of the PP element and distal and volar to the center of rotation of the PIP joint; thus, implantation does not disrupt the attachment sites of the collateral ligaments or the attachment site of the volar plate. This design wherein the lateral dimension of the dorsal portion of the bicondylar distal head of the PIP element is smaller than the lateral dimension of its volar portion allows the lateral bands of the extensor expansion to move normally during flexion/extension. The volar plane of this proximal surface lies at an angle of less than 45° from the long axis of the implant, preferably about 30°, which orientation minimizes the extraction force created by eccentric joint reaction forces.

The MP element's proximal articular head has a generally elliptical outline, except for a relief means on its dorsal aspect, and it has a biconcave articular surface. This dorsal relief means accommodates the ICP and assures that the motivating and stabilizing function of the median band is maintained. The head is shaped to be thinner along its volar aspect so as not to disrupt the attachment sites of the collateral ligaments, to avoid interference with the volar plate during flexion and to provide a free path for the collateral ligaments. The relief means on the dorsal aspect of the MP element is proportioned to provide a free path for the median band of the extensor expansion to wrap around the articular head of the adjacent PP element. Furthermore, because the median band has a free path, the ICP of the median band will fill the intercondylar notch of the proximal phalangeal member and laterally stabilize the median band during flexion-extension. Also, the MP element's head has two dorsal protrusions that are located at a boundary of the biconcave articular surface and shaped to generally extend over the condyles of the articular surface of the head of the PP element a sufficient distance so as to resist subluxation-dislocation of the middle phalangeal bone in the volar direction when the finger is in extension.

The improved prosthetic PIP joint realizes the aforementioned objects, features and advantages in a manner that is clearly evident from a thorough consideration of the detailed description when taken in conjunction with the drawings wherein there is shown and described certain preferred embodiments incorporating various features of the invention.

BRIEF DESCRIPTION OF THE DRAWINGS

FIG. 1 is schematic view, partially in section, of the human hand bone anatomy showing the general placement of an artificial PIP joint.

FIGS. 2a and b are side elevation and dorsal views illustrating the arrangement of the extensor expansion, collateral ligaments of the normal PIP joint when the proximal phalangeal bone and the middle phalangeal bone are in full extension, with the distal phalanx at the top.

DETAILED DESCRIPTION OF THE PREFERRED EMBODIMENTS

The present invention is directed to an interphalangeal joint prosthesis and to a method for replacement of a diseased or damaged human finger joint. The preferred prosthesis is designed for permanent implantation to take the place of the PIP joint.

Figures 1, 2A, 2B:
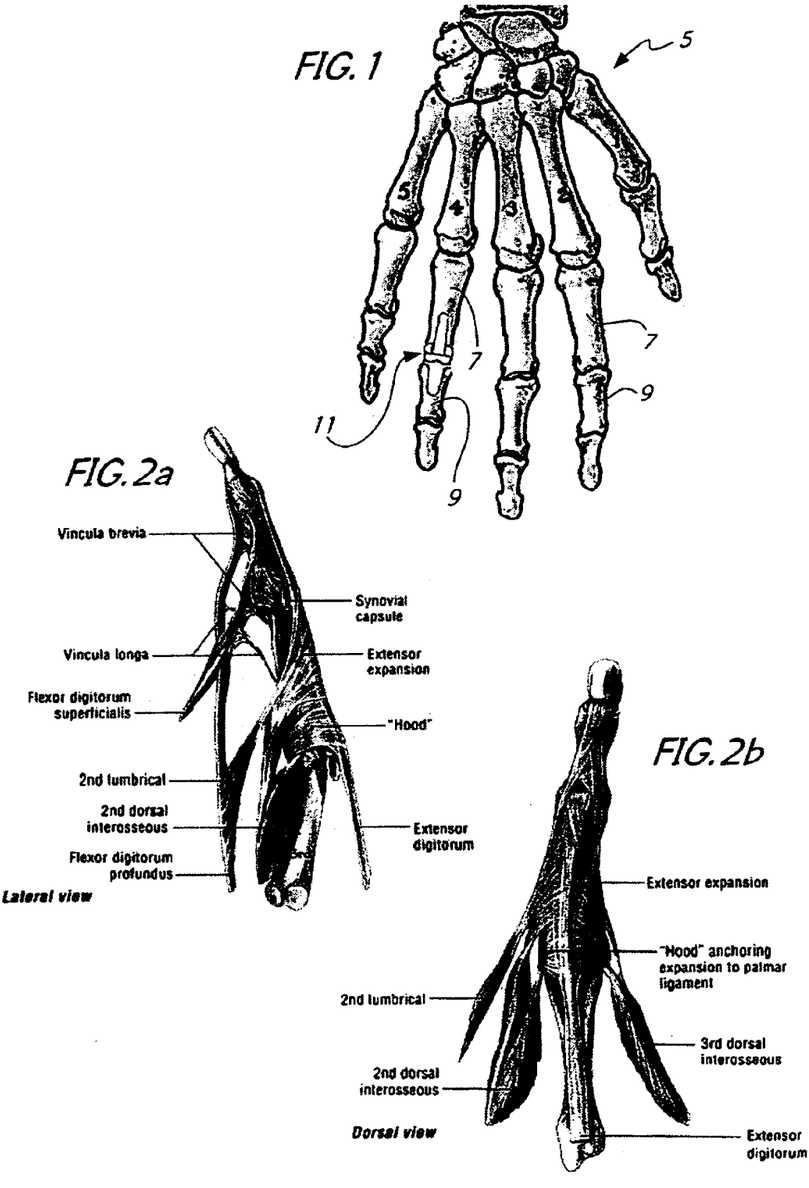
Figure 3:
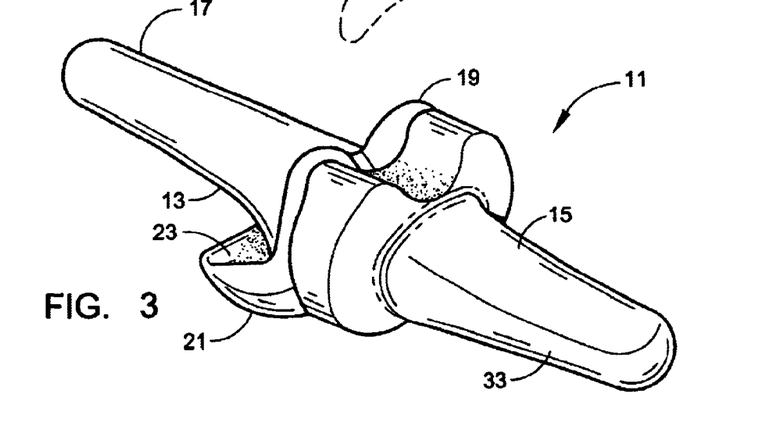
FIG. 3 is a perspective view of a prosthetic PIP joint embodying various features of the invention showing the proximal phalangeal element and middle phalangeal element in full extension and particularly showing the lateral side of the head of the proximal phalangeal element and the relief which is cut dorsally in the head of the middle phalangeal element.

In FIG. 1, a human right hand 5 is shown from the dorsal perspective, with the proximal phalanx 7 and the middle phalanx 9 of the ring finger (labeled 4) containing a schematic representation of a PIP joint 11. As best seen in FIG. 3, the PIP joint prosthesis 11 includes a first or PP element 13 that articulates with a second or MP element 15. The PP element 13 is implanted in and replaces distal end of the proximal phalanx 7, and the MP element 15 is implanted in and replaces the proximal end of the middle phalanx 9.

The PP element 13 includes a stem portion 17 which is formed as an integral portion with a head portion 19. The head portion has a convex bycondylar surface 21 and a rear or proximal surface 23 that is formed by two intersecting planes.

Figure 3A:
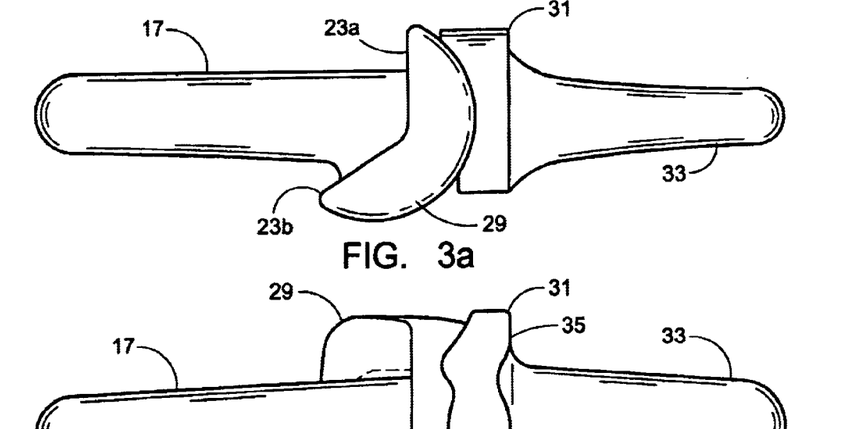
FIG. 3a is a side elevation view of the PIP joint of FIG. 3.
Figures 3B, 3C, 3D:
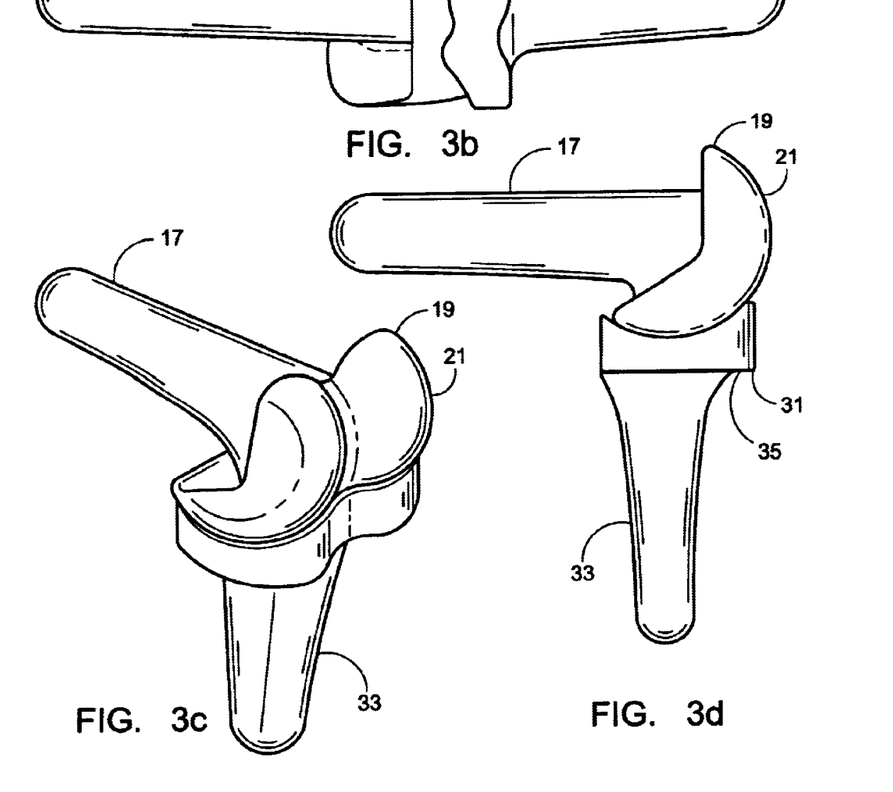
FIG. 3b is a top or dorsal view of the PIP joint of FIG. 3.
FIG. 3c is a perspective view of the PIP prosthetic joint of FIG. 3 showing the proximal phalangeal element and middle phalangeal element flexed 90°.
FIG. 3d is a side elevation view of the PIP joint as shown in FIG. 3c.

As best seen perhaps in FIGS. 3a–3d and FIGS. 5 and 5a, the PP element 13 has a longitudinal axis (extending horizontally in FIG. 3a) that forms the central axis of the stem 17, and the rear surface 23 of the head 19 is formed by a first plane 23a that is substantially perpendicular to the longitudinal axis. This plane extends past the longitudinal axis a distance equal to about 20% of the radius of the largest arc on the convex condylar surface (see FIG. 6a), where it intersects a second oblique plane 23b which is oriented at an angle of between about 110° and about 130° thereto. It will be understood that the proximal phalanx of the patient will be cut to have two complementary surfaces that will match precisely with these two intersecting planes. The stem portion 17 may have any suitable cross-sectional shape, for example circular, generally rectangular or polygonal; preferably, it has a generally trapezoidal shape decreasing in width uniformly along its length as best seen in FIGS. 3b and 6b. The stem portion 17 is received within the marrow or medullary cavity of the proximal phalanx of the patient.

Figures 5, 5A:
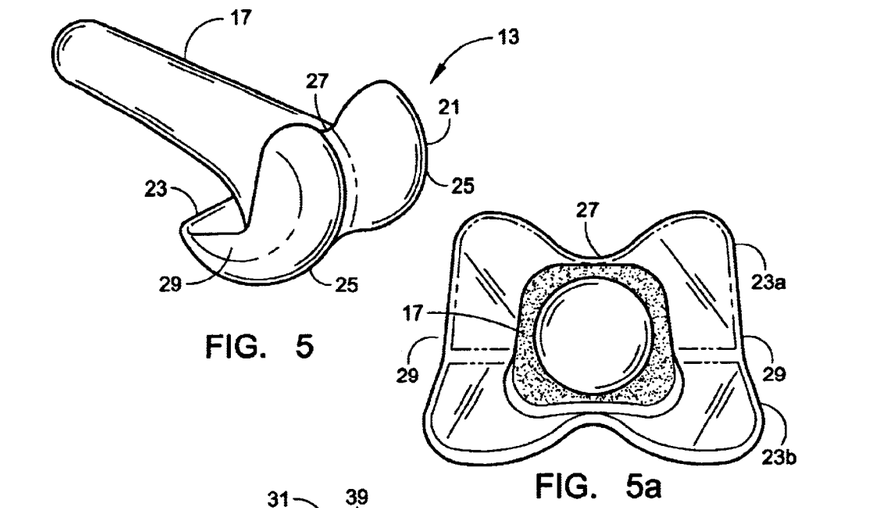
FIG. 5 is a perspective view of the proximal phalangeal element of FIG. 3.
FIG. 5a is a perspective view of the proximal phalangeal element of FIG. 3.

The articulating head surface 21, as best seen perhaps in FIG. 5, is formed with two surfaces that are mirror images of each other that are located on opposite sides of the plane of symmetry which is a vertical (dorsal to volar) plane that includes the longitudinal axis of the element 13. This convex articulating surface in essence has a pair of condyles 25 that are separated by a central valley 27. The distal or articulating surface of the head 19 is preferably uniform in its shape and extends for about essentially 200° of arcuate surface as can be best seen from FIGS. 6 and 6a; the limits of the surface are defined by the location of the two planes 23a and plane 23b which are both offset distally and/or volarly from the axis of rotation. Each of the two condyles is uniform and can be generated by the rotation of a curved line about a horizontal axis (see FIG. 6a with reference to R1). The valley 27 in between is also smoothly shaped as represented by the radius R4 of FIG. 6c and results in the creation of a notch in both planes 23a and 23b.

The head 19 has a pair of lateral surfaces 29 that are preferably planar and that are defined by planes that are parallel to the longitudinal axis of the element. However, these planes are not parallel to each other but are oriented at equal angles to the plane of symmetry of the element 15 so as to intersect along a line that lies within the plane of symmetry, which line is located substantially above the head itself. These planes are preferably oriented at an angle between about 7° and about 17° to the plane of symmetry, and preferably about 10°, and this slope to the head (best seen in FIG. 5a) provides clearance for the collateral ligaments as explained in more detail hereinafter.

Figure 4:
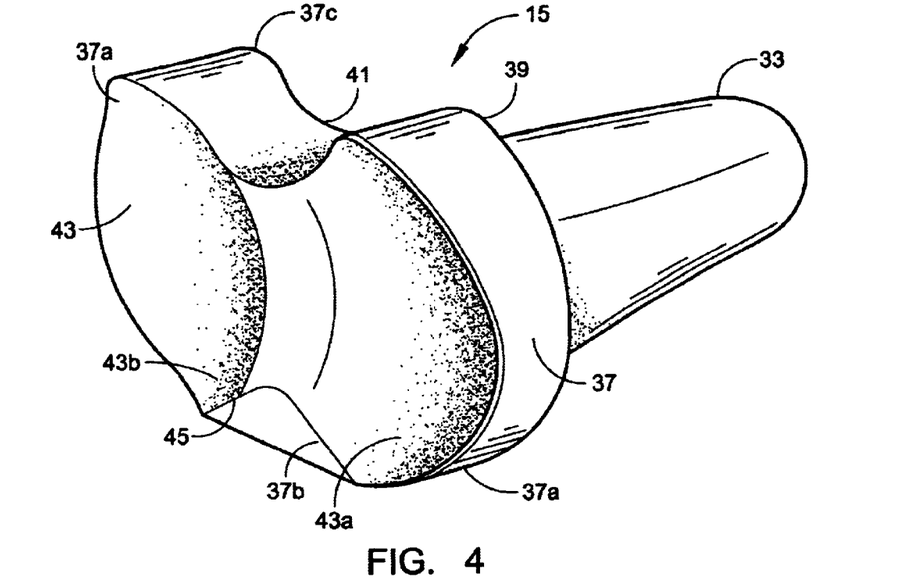
FIG. 4 is a perspective view of the middle phalangeal element of FIG. 3.
Figure 4A:
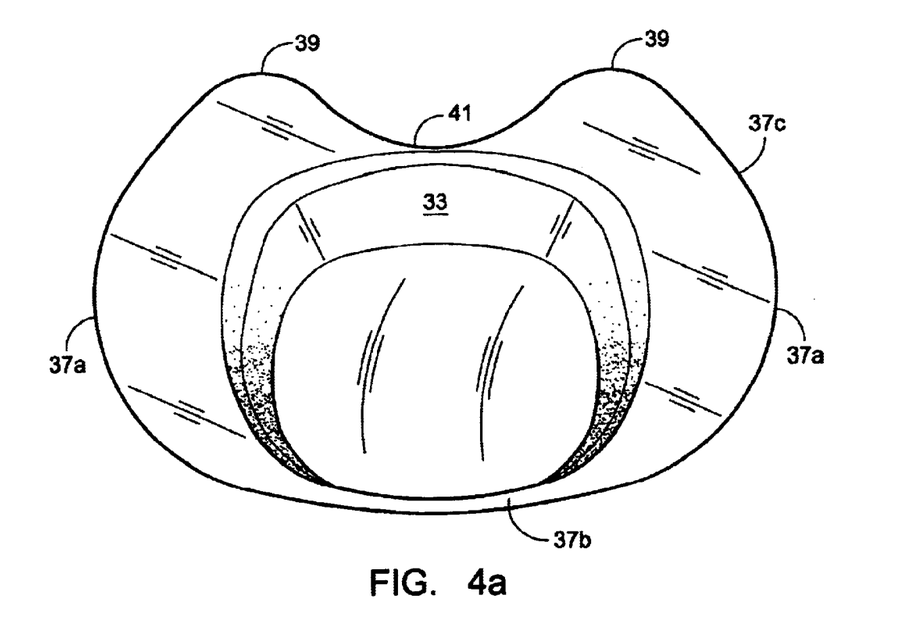
FIG. 4a is a rear view of the element of FIG. 4.
Figure 6:
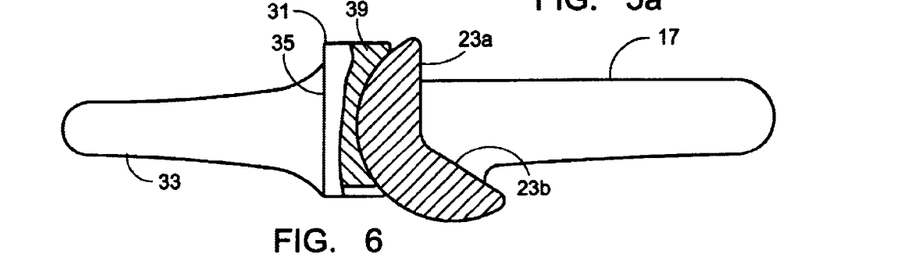
FIG. 6 is a side elevation of the replacement PIP joint shown in FIG. 3a that is partially in section through one of the condylar contact planes.

The second or MP element 15 is similarly formed with a head 31 and a stem 33 as best seen perhaps in FIG. 4. The stem 33 can generally be shaped as mentioned hereinbefore, but as shown in FIGS. 3a, 3b and 4a, it preferably has a generally cross-section that is somewhat broader than the corresponding dimension of the stem 17. As best seen in FIG. 6, the longitudinal axis of the MP element is offset volar to the longitudinal axis of the PP element. The amount of the offset is between about 5% and 15% and preferably about 10% of the radius R1 which is the largest radius of curvature of the condyle. This offset is advantageous because this offset increases the degree to which the extensor expansion wraps around the head of the PP element, and this allows the finger to extend more easily. The stem 33 likewise defines the longitudinal axis of the distal element 15, and as best seen in FIG. 3a, the longitudinal axes of the PP and MP elements are essentially coaxial. The head 31 has a distal or rear surface 35 that is essentially planar; however, the region that immediately surrounds the generally trapezoidal cross-section stem is blended smoothly into the rear surface 35 with fillets of small radii, as best seen in FIG. 3a and FIG. 6. The head 31 has a rectilinear peripheral surface 37 which is arcuate in its outline, having a pair of side surfaces 37a which generally constant radius, a volar surface 37b of greater radius that blends into the two side surfaces, and a dorsal surface 37c that is formed with a pair of projections 39 separated by a broad central notch 41. In addition, as best seen in FIGS. 3a and 6, the dorsal region of the head is substantially thicker than the volar region for a reason to be explained hereinafter.

The head 31 has a proximal or front surface 43 that is biconcave providing a pair of sockets 43a to receive the condyles 25 of the PP element head 19, which sockets 43a are separated by a smooth ridge 43b located along a vertical (or dorsal to volar) plane of symmetry that contains both longitudinal axes of both elements. As explained in detail hereinafter, although the head 31 is proportioned so as to dominate the head 19 of the PP element in full extension, the proportioning of the notch 41 is such that it does not interfere with the finger ligaments in this area, particularly the median band and the ICP.

The proximal surface 43 of the element 15 is preferably formed with a chamfer 45 in the volar region which provides clearance for ligaments and the attachment to the volar plate as well allowing articulation of the MP element head about the PP element head in full flexion.

Figure 8:
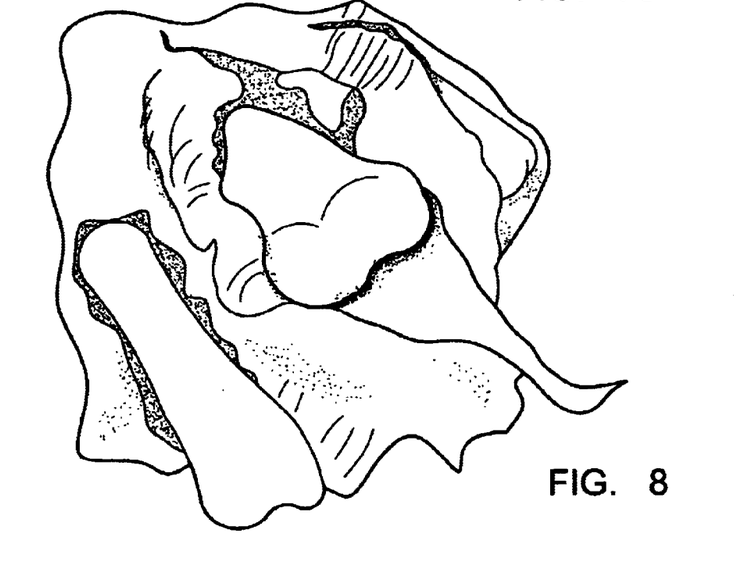
FIG. 8 is a picture of the ICP of the median band of the extension expansion dissected and reflected distally.
Figure 9:
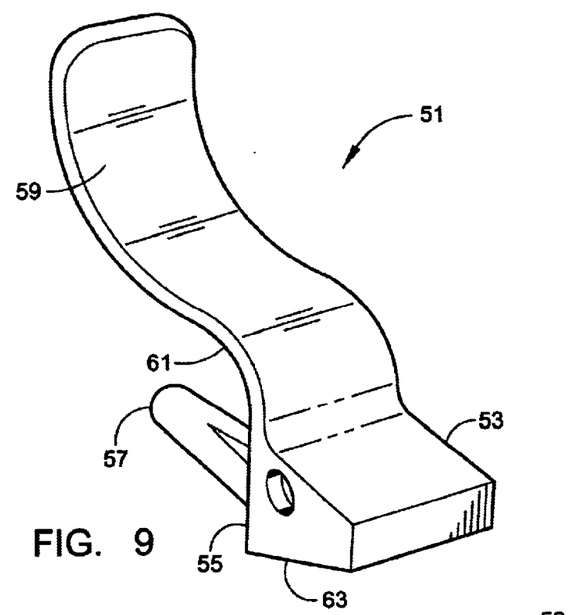
FIG. 9 is an illustration of a preferred cutting guide that may be used in preparing a deteriorated joint for an implant.
Figures 10, 10A, 12:
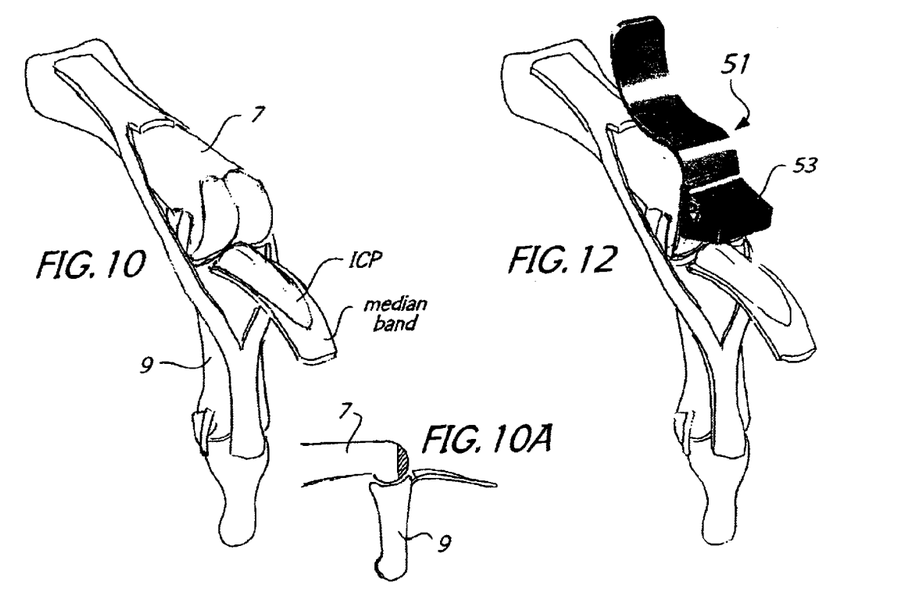
FIGS. 10–13 are perspective and exploded perspective views which show the surgical preparation of a deteriorated PIP joint for implantation of a prosthetic implant at the distal end of the proximal phalanx.
FIGS. 10A and 11A are side schematic views that show the proximal and middle phalanges as they appear, respectively in FIGS. 10 and 11, with the regions about to be cut indicated by crosshatching.

The locations of the fan-like collateral ligaments, the cord-like collateral ligaments, and the retinacular ligaments were previously described, along with those of the extensor expansion and certain tendons, such as the stensor digiti minimi. These are variously illustrated in FIGS. 2a through 2d and in FIGS. 7a through 8. In order to replace a deteriorated PIP joint, for example, the surgeon would open the finger dorsally to provide access to the median band which is severed at a proximal location and then peeled away as shown in FIGS. 8 and 10 to expose the deteriorated joint. The two planar cuts are then made to remove the distal end of the proximal phalanx 7, as by making a first cut perpendicular to the longitudinal axis thereof and then a second cut volar thereof at an angle of about 120° thereto. A guide 51 for assisting in making such cuts is illustrated in FIG. 9. If carefully performed, the removal can be carried out so as not to disturb the collateral ligaments, the retinacular ligaments or the volar plate.

Figures 11, 11A, 13:
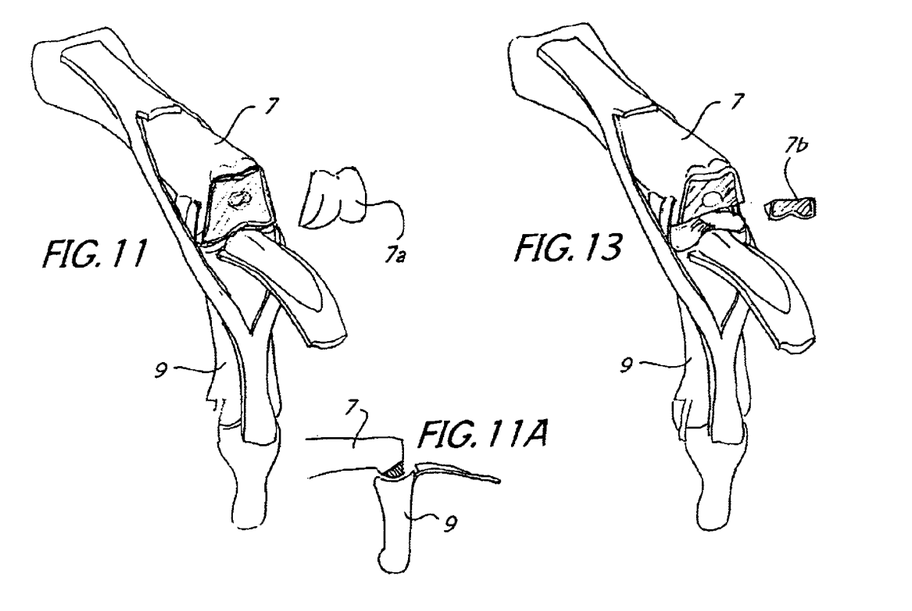

To employ the cutting guide 51, the surgeon makes a first cut perpendicular to the longitudinal axis of the proximal phalanx 7. This procedure is shown in FIGS. 10 and 11 where the median band has been severed and then peeled back with the two phalangeal bones 7, 9 of the PIP joint shown in 90° flexion. In the next step, the distal end of the proximal phalanx 7 (which is shown cross-hatched in FIG. 10A) is removed by a cut perpendicular to the longitudinal axis of the proximal phalanx. The result is shown in FIG. 11 where the severed tip 7a is shown in exploded perspective, leaving a flat distal end face on the proximal phalanx 7. The medullary canal is then broached to prepare for the insertion of the cutting tool 51 which assists in the removal of the volar portion of the distal end of the proximal phalanx, which is shown cross-hatched in FIG. 11A.

Figure 14:
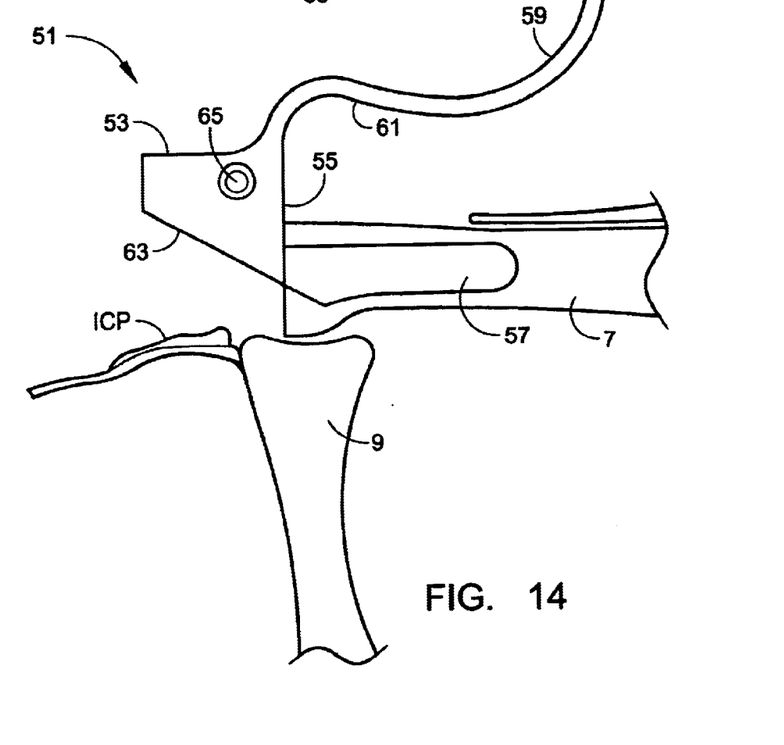
FIG. 14 is an enlarged right side view of FIG. 12 showing the cutting tool in elevation and the proximal phalanx in section.

As best seen in FIGS. 9 and 14, the cutting guide 51 has a head 53 having a flat rear surface 55 which, in its operative position, will abut the flat surface that has been cut at the distal end of the proximal phalanx 7. Extending perpendicularly from the rear surface 55 is a stem 57 which is shaped to enter the medullary canal. A curved handle 59 is integral with the head 53 and extends dorsal and rearward therefrom having a curved bend 61 downward and then a reverse bend upward. The handle 59 is designed to allow the surgeon to easily fully insert the stem 57 into the proximal phalanx so that the flat rear surface 55 abuts the cut distal end. An undersurface 63 of the head 53 is cut at an angle of precisely 60° with the flat rear surface 55 of the head to serve as a guide for making the cut by which the volar slice (see 7b in FIG. 13) is removed in order to leave two flat surfaces at the distal end of the proximal phalanx 7 that are precisely at an angle of 120° to each other. The slice 7b is seen in FIG. 13 where the cutting guide 51 has been removed after the cut has been made, exposing the proximal end of the middle phalanx 9 for the next step in the preparation for the joint implantation. The head 53 also contains a smooth bore 65, having frustoconical edges at each end, which extends laterally through the head parallel to the rear surface 55. The bore 65 allows the surgeon to easily extract the guide from the medullary canal by inserting a small tool and pulling outward at a location close to the longitudinal axis of the stem 57.

The proximal end of the middle phalanx 9 is prepared for the implant in a manner which preserves the dorsal tubercle of the proximal end of the middle phalanx by removing the articular surface in the region therebelow in a way which does not disturb the attachment of the ICP to the dorsal tubercle. Any suitable method of removal can be used; for example, by simple hand burring or by making two shallow bores into the face which flank the medullary canal and are shaped to generally complement the peripheral outline of the head of the MP element in the location of its lateral edges 37a and then suitably burring away the volar region intermediate thereto. A slight amount of shaping would then be carried out as needed to accommodate the head in the region of the notch 41. Once the appropriate erosion has been effected to accommodate the shape of the flat distal region of the head 31, the medullary canal is broached to accommodate the stem 33. With both of the elements installed, the joint of the finger is reassembled by stitching the proximal end of the median band back into position and by closing the finger, dorsal of the joint.

It should be apparent from the foregoing that the sloping side faces 29 of the head 19 of the PP element provide important clearance for the fan-like and cord-like ligaments and the lateral bands of the extensor expansion. Moreover, the retention of the dorsal tubercle of the middle phalanx 9 where the ICP is attached and the shaping of the head 31 in the notch region so that the portion that protrudes avoids any interference during flexion of the joint permit the finger to function in a totally normal fashion after the prosthetic joint 11 has been installed.

Figure 7A:
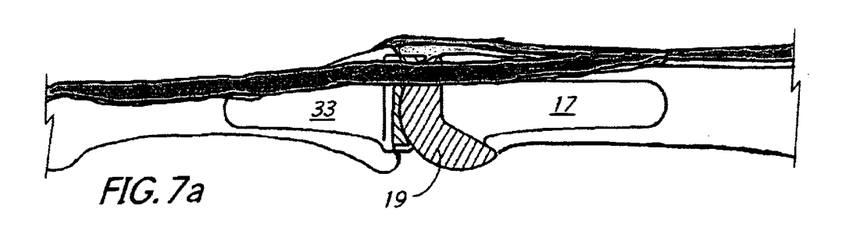
FIG. 7a is a diagrammatic side view of a proximal phalangeal bone and a middle phalangeal bone in full extension, with the replacement PIP joint of FIG. 3 inserted therein and shown in partial section through one of the condylar contact planes.
Figure 7B:
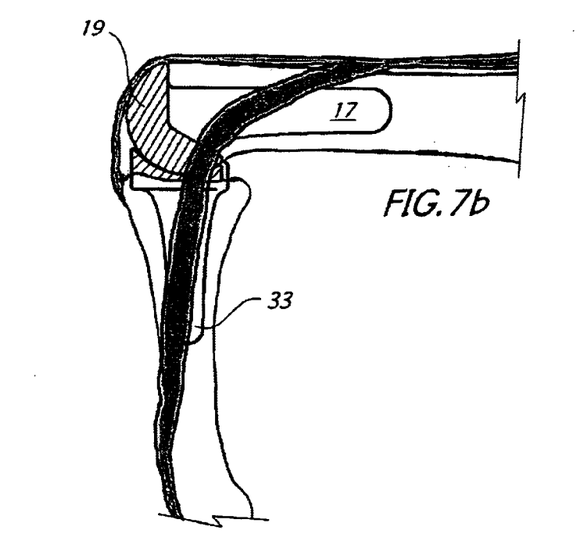
FIG. 7b is a side view in partial section through one of the condylar contact planes showing the joint of FIG. 7a in 90° of flexion.

FIG. 6 and FIG. 7a illustrate the joint 11 in full extension and show the advantageous presence of the projections 39 at the volar region of the head 31 of the MP element which result from the proportioning of the head 31 to be thicker in the dorsal region than in the volar region. As a result, the projections 39 overlie the two condyles 25 in a dorsal direction and establish a dorsal prominence which resists any volar subluxation-dislocation of the middle phalangeal bone 9. Similarly, the advantage of the mating of the distal end of the proximal phalangeal bone 7 with the rear face of the PP element defined by the two intersecting planes is also apparent. Because the lower or volar plane 23b is at an angle of less than 45° from the longitudinal axis of the implant, preferably at an angle of about 30° therefrom, this orientation minimizes the extraction force created by the eccentric joint reaction forces.

The relative positioning and proportioning of the two articulating surfaces is described hereinafter with respect to various of the figures including FIGS. 6 through 6d and FIGS. 7a through 7d. Broadly, the condylar articulating surfaces are designed to avoid the establishment of a dry joint, and it is important that they are not congruent and preferably they are not spherical surfaces but the latter is not critical. Moreover, by careful proportioning of these noncongruent surfaces, it has been found that sets of PP elements 13 of two or three different sizes can acceptably be used in combination with an MP element of a certain size, and vice versa, which is referred to as the ability to "size-up" and "size-down" a particular pair of mating PP and MP elements. This desirable result is achieved by designing the interphalangeal joint so that the contact normally occurs only at a single point on each of the concave cavities and along a corresponding line on the respective convex mating surface as a result of relative movement therebetween which occurs as the joint moves to and from between a position of full extension and a position of, for example, 90° flexion, as shown for example in FIGS. 3a and 3d, as well as in FIGS. 7c and 7d.

Figure 6A:
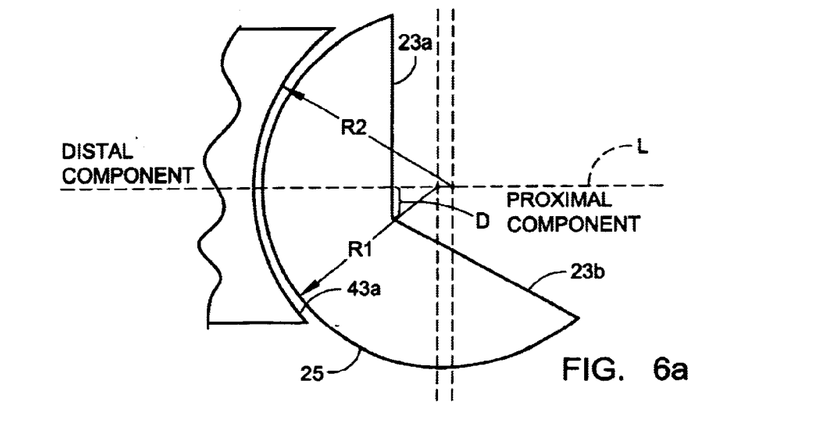
FIG. 6a is an enlarged fragmentary diagrammatic sectional view illustrating the relative proportioning of the articular contact surfaces shown in FIG. 6.
Figure 6B:
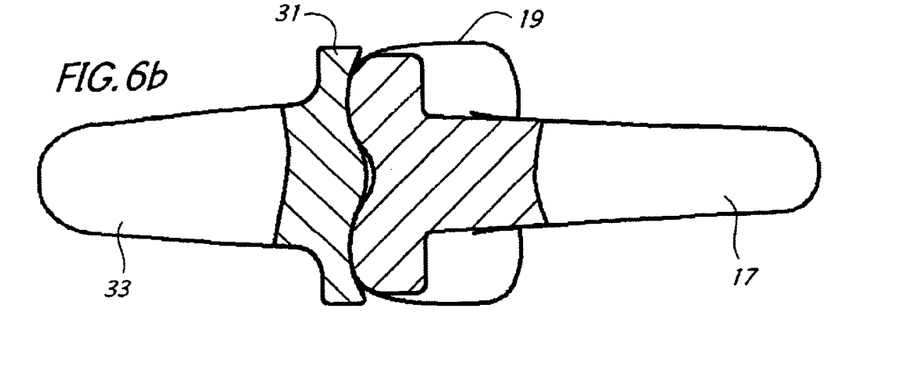
FIG. 6b is a top or dorsal view of the replacement PIP joint shown in FIG. 3b with portions shown in section.
Figure 6C:
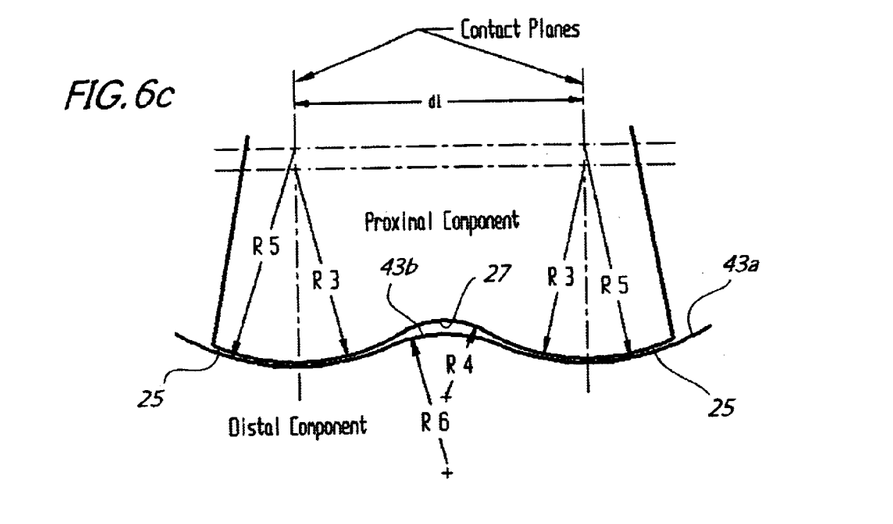
FIG. 6c is an enlarged fragmentary diagrammatic sectional view illustrating the relative proportioning of the articular contact surfaces from the perspective shown in FIG. 6b.
Figure 6D:
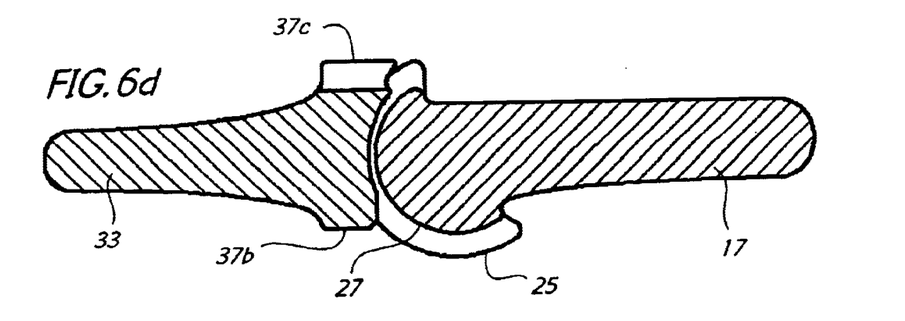
FIG. 6d is a side sectional view through the medial plane of the replacement PIP joint shown in FIG. 3a showing the region of the intercondylar notch.

The specifics of the noncongruent surfaces will be best seen from FIGS. 6a and 6c where the various radii of curvature are illustrated. In FIG. 6a, the horizontal line marked L represents the longitudinal axis of the joint 11 which is also preferably the longitudinal axis of the PP element 13, the axis of the MP element being offset volar therefrom. FIG. 6a is a schematic and shows that the greatest radius of curvature, R1, of the surface on the convex condyle is less than the corresponding radius of curvature R2 of the concave cavity of the distal element. It also illustrates the distance labeled D, the line of intersection between the two planes 23a and 23b that define the rear or proximal surface of the PP element 13 is displaced volar of the longitudinal axis.

Similarly, the FIG. 6c diagrammatic view illustrates the respective proportioning of the two articular surfaces in a horizontal plane, perpendicular to the vertical plane along which FIG. 6a was taken. In this view, both of the condyles 25 are shown in order to illustrate the dimensioning of the smooth valley 27 and ridge 43b that lie centrally thereof, along the plane of symmetry of the implant. Again, it can be seen that the radius of curvature R3 in the horizontal plane of the convex condyle is smaller than the radius of curvature R5 of the concave cavity 43a. Likewise, comparing the curved surfaces of the ridge and valley shows that the valley 27 is formed with a radius of curvature R4 that is substantially less than the radius R6 of the ridge 43b. Because the radius R3 is substantially less than the radius R1, the surface of the convex condyle is not spherical. Likewise, the radii of curvature R2 and R5 of the concave cavities 43a in the proximal surface 43 of the MP element 15 are different in this illustrated embodiment. This arrangement assures that there will be adequate space between the articular surfaces of the elements 13 and 15 to permit the intrusion of synovial fluid, thus guarding against the disadvantageous creation of a dry joint.

The specific noncongruent shapes of the articular surfaces of the joint 11 also lend themselves to the accommodation of a PP element by a MP element of slightly different size in order to best fit a patient's anatomy. As illustrated in FIG. 6c, the contact between the two articular surfaces will occur in two parallel planes, referred to as contact planes, spaced apart from each other by a distance d1. To facilitate implantation in joints of patients having knuckles of different sizes, implants 11 may be made in sets of different size components, for examples sizes A through F, with size A being the smallest and size F the largest. In each of these sets, the distance d1 with respect to the PP elements and the MP elements for each size will stay exactly the same; however, the length of the radii R1 and R2 will grow larger from set A to set F for example. However, because of this unique construction and proportioning, a PP element from size C, for example, could be acceptably mated with an MP element from size B, C or D (or vice versa) because the relative curvature of the condyle will be such that for even one size greater, or lesser, as the case may be, the radius R1 of curvature of the condyle will be less than the radius R2 of the curvature of the cavity so that the sliding contact during articulation will still be totally acceptable. In addition, because the sets increase in size, the head of the PP element, i.e. the distance between the lateral sides 29 will grow slightly as will the width and height of the head 31 of the MP element without affecting the curvature of the articulating surfaces.

In summary, the ability to size-up and size-down is achieved by means of controlling the location and magnitude of the radii of curvature of the articular surfaces of the bicondylar joint prosthesis as follows: (1) the distance between the contact planes (d1) shown in FIG. 6c is kept constant for the PIP joint different sizes, (2) radius R5 shown in FIG. 6c is always greater than radius R3, and radii R5 and R3 do not change between sets, and (3) radius R2 shown in FIG. 6c is always greater than radius R1. Proximal and distal joint components of the different sizes will mate and articulate with each other as long as the above criteria are met. This arrangement thus provides the surgeon with a substantial advantage. It enables him to have a choice when, as is often the case, the anatomy of a particular patient is such that both components of any one size would not be preferable; with this arrangement, the surgeon is allowed to either size-up or size-down as necessary and thus provide a superior ultimate fit.

Figure 7C:
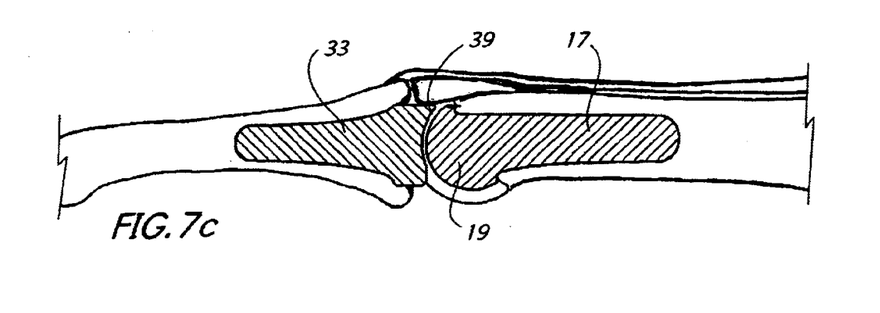
FIG. 7c is a view similar to FIG. 7a taken centrally along the longitudinal axis of the PIP joint, with the retinacular ligament removed, illustrating the region of the intercondylar notch of the head of the PP element and the position of the median band and the ICP.
Figures 7D, 7E:
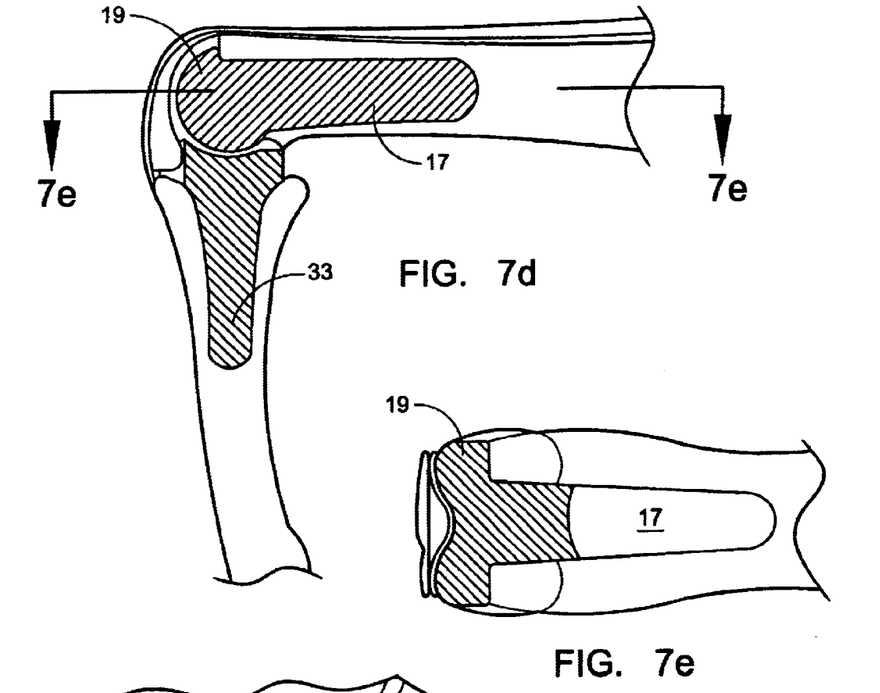
FIG. 7d is a side view in partial section through the medial plane of a proximal phalangeal bone and a middle phalangeal bone in 90° of flexion with the replacement PIP joint of FIG. 3 inserted therein and with the retinacular ligament removed.
FIG. 7e is a section view taken along line e—e of FIG. 7d showing the ICP filling the intercondylar notch of the head of the proximal phalangeal element and the relative position of the lateral bands of the extensor expansion.

Once the joint implant 11 has been installed and the finger returned to its original orientation and sutured, the situations illustrated in FIGS. 7a to 7d are attained. For example, with respect to FIG. 7a, it can be seen how the sloping lateral surfaces 29 of the head 19 of the PP element will provide clearance for the retinacular ligaments, and that the median band will be excellently received in the valley 27 between the condyles 25 of the head of the PP element and in the notch 41 in the head of the MP element. When the finger is moved from a position of full extension (shown in FIG. 7a) to the position of flexion (shown in FIG. 7b), the ligaments slide smoothly along the sloping surfaces 29 of the head and without any substantial interference. In FIG. 7c, where the ligaments are removed for illustration purposes and the sectional view is taken along the plane of symmetry of the implant, it can be seen that the thickest portion of the ICP is excellently accommodated in the notch 41 of the head and that the location of attachment of the median band to the middle phalanx 9 remains undisturbed. This desirable objective is a result of creating a cavity in the proximal end face of the middle phalanx 9 and correctly proportioning the notch 41 in the dorsal surface of the head 31. In the companion FIG. 7d, which shows the joint in 90° flexion, the ICP resides in the valley 27 between the condyles where it is neatly accommodated as shown in FIG. 7e, which is a section view taken generally along the line e—e of FIG. 7d.

The PP and MP elements 13, 15 are preferably made of biocompatible materials having a modulus of elasticity in the range of that of natural living bone, one example of which is a structure made of a graphite substrate coated with pyrocarbon. More importantly, the elements 13 and 15 are made of materials having sufficient hardness that they will not distend significantly under the normal load to which they will be expected to be subjected during use. Again, pyrocarbon-coated graphite meets this specification and also provides exterior surfaces that exhibit good wear resistance so that they will retain their original surface contours following years of implantation. However, if additional strength were felt to be desirable, the elements might be formed of pyrolytic carbon that has been deposited upon carbon—carbon fiber composite material that exhibits higher tensile strength than graphite.

Although the invention has been described with respect to certain preferred embodiments, various changes and modifications as would be obvious to one having the ordinary skill in the art may be made without departing from the scope of the invention which is defined solely by the appended claims. For example, although the interphalangeal joint has been described with respect to the replacement of a PIP joint, it should be understood that by changing the relative sizes of the elements 13, 15, they may also be readily adapted for use in a DIP joint. The disclosures of all U.S. patents to which reference has herein been made are expressly incorporated by reference. Particular features of the invention are emphasized in the claims which follow.

What is claimed is:

1. An interphalangeal joint prosthesis comprising
   first and second elements having mating heads that allow smooth articulation generally within a single plane extending dorsal to volar,
   said first element head having (a) a proximal surface defined by two intersecting planes which will abut complementary surfaces cut onto one phalanx of a patient's finger, (b) a stem portion that extends longitudinally therefrom which is proportioned to be received within the medullary cavity of the one phalanx, and (c) a convex bicondylar articulating surface with a central valley that extends as a continuous curve from a dorsal intercondylar notch in its dorsal surface to a region volar of said stem portion,
   said second element head having (a) a biconcave articulating surface for its proximal surface, which mates with said convex articulating surface of said first element and engages said surface at points along two lines of contact in two parallel planes and which surface includes a central ridge that is aligned with but spaced from said central valley of said convex articulating surface and (b) a stem portion that extends longitudinally therefrom and that is proportioned to be received within the medullary cavity of an adjacent phalanx, and
   said second element head also having a notch in a dorsal surface thereof which is centrally located and aligned with the longitudinal axis of said second element so as not to disturb attachments to the patient's dorsal tubercle of the proximal head of the middle phalanx or the function of the patient's median band of the patient's extensor expansion.

2. The interphalangeal joint prosthesis according to claim 1 wherein said first element bead has lateral surfaces defined by a pair of planes aligned parallel to the longitudinal axis of said first element and oriented at an angle of between about 7° and about 17° from the vertical so that the dorsal region of said head is narrower than the volar region thereof.

3. The interphalangeal joint prosthesis according to claim 1 wherein said two intersecting planes which define said proximal surface are aligned at an angle of between about 110° and 130°.

4. The interphalangeal joint prosthesis according to claim 3 wherein said two planes intersect at a line that lies volar of the longitudinal axis of said first element.

5. The interphalangeal joint prosthesis according to claim 3 wherein said two planes intersect at a line that lies distal and volar to a central point about which the joint rotates.

6. The interphalangeal joint prosthesis according to claim 3 wherein the volar plane of said two planes is aligned at an angle of less than 45° to the longitudinal axis of the first element.

7. The interphalangeal joint prosthesis according to claim 3 wherein the volar plane of said two planes is aligned at an angle of about 30° to the longitudinal axis of the first element.

8. The interphalangeal joint prosthesis according to claim 1 wherein said head of said second element is generally elliptical in lateral outline except for said dorsal notch.

9. The interphalangeal joint prosthesis according to claim 1 wherein said second element head is thicker longitudinally in the dorsal region than in the volar region and dominates said first element head when the joint is aligned in full extension.

10. The interphalengeal joint prosthesis according to claim 1 wherein said convex bicondylar articulating surface of said first element head has one uniform radius of curvature in the dorsal to volar plane and a different radius of curvature in a lateral plane perpendicular thereto, and wherein said biconcave surface of said second element likewise has one uniform radius of curvature in the dorsal to volar plane and a different radius of curvature in the lateral plane perpendicular thereto.

11. A method for treating a deteriorated PIP joint of a human finger of a patient, which method comprises the steps of
(a) removing an articular portion at the distal end of the proximal phalanx of said deteriorated joint in a manner so as not to disturb the collateral ligament attachment sites thereof by cutting the proximal phalangeal bone along a plane perpendicular to the longitudinal axis of the bone and by making another cut of said bone at a location volar of said longitudinal axis along a plane aligned at an angle of between about 110° and about 130° to said perpendicular plane, said two planes intersecting along a line volar of said longitudinal axis;
(b) removing an articular portion of the proximal end of said middle phalangeal bone of said deteriorated joint in a manner so as not to disturb the sites of attachment of collateral ligaments thereto; and
(c) replacing said distal end of said proximal phalangeal bone and said proximal end of said middle phalangeal bone with an interphalangeal joint prosthesis having first and second elements which have mating heads that allow smooth articulation generally within a single plane extending dorsal to volar, and which have rear surfaces that mate substantially flush with the surfaces where said removals took place at the respective ends of said proximal phalangeal bone and said middle phalangeal bone, said first and second elements each having stem portions integral with said respective heads which are received within the respective medullary cavity of the respective phalangeal bone, said first element head having a convex bicondylar articulating surface with a central valley that extends as a continuous curve from a dorsal intercondylar notch in its dorsal surface to a region volar of said stem portion, and said second element having a biconcave articulating surface for its proximal surface which mates with said convex articulating surface of said first element, and also having a notch in its dorsal surface which is centrally located and aligned with the longitudinal axis of said second element so as not to disturb attachments to the patient's dorsal tubercle of the proximal head of the middle phalangeal bone or disturb the function of the median band of the patient's extensor expansion.

12. The method according to claim 11 wherein said two cuts intersect at a line that will lie volar and distal to the central point about which said first and second element heads rotate.

13. The method according to claim 11 wherein said first element head has lateral surfaces defined by a pair of planes aligned parallel to the longitudinal axis of said first element and oriented at an angle of between about 7° and about 17° from the vertical so that the dorsal region of said head is narrower than the volar region thereof.

14. The method according to claim 11 wherein said second element head is longitudinally thicker in the dorsal region than in the volar region and dominates said first element head when the joint is aligned in full extension.

15. A set of interphalangeal joint prostheses including groups of first elements and groups of second elements of different sizes which elements have mating heads that allow smooth articulation generally within a single plane extending dorsal to volar,
each said first element head having (a) a proximal surface defined by two intersecting planes which will abut complementary surfaces cut onto one phalanx of a patient's finger, (b) a stem portion that extends longitudinally therefrom which is proportioned to be received within the patient's medullary cavity of the one phalanx, and (c) a convex bicondylar articulating surface with a central valley that extends from a dorsal intercondylar notch in its dorsal surface to a region volar of said stein portion,
each said second element head having (a) a biconcave articulating surface for its proximal surface, which mates with said convex articulating surface of said first element, and (b) a stem portion that extends longitudinally therefrom and that is proportioned to be received within the medullary cavity of an adjacent phalanx, and
said convex bycondylar articulating surface of each said element having one radius of curvature in the dorsal to volar plane and a different radius of curvature in a lateral plane perpendicular thereto, and said biconcave surfaces of said second element likewise having one radius of curvature in the dorsal to volar plane and a different radius of curvature in the lateral plane perpendicular thereto,
with the proviso that the radii of curvature in the lateral plane is the same for all sizes of convex condyles in the set and is the same for all concave articulating surfaces in the set, with the radius of curvature of the condyles being lesser, and with the further proviso that the radii of curvature in the dorsal to valet planes increases from size to size, provided however, that the radius of curvature of the cavity in any one size will be larger than the corresponding radius of curvature of the condyle for that size and for the next larger size.

16. The set of interphalangeal joint prostheses according to claim 15 wherein said convex bicondylar and said biconcave articulating surfaces engage at points along two lines of contact in two parallel planes.

* * * * *

UNITED STATES PATENT AND TRADEMARK OFFICE
CERTIFICATE OF CORRECTION

PATENT NO.    : 6,699,292 B2
DATED         : March 2, 2004
INVENTOR(S)   : William F. Ogilvie et al.

It is certified that error appears in the above-identified patent and that said Letters Patent is hereby corrected as shown below:

Column 12,
Line 53, "bead" should be -- head --; and

Column 14,
Line 54, "valet" should be -- volar --.

Signed and Sealed this

Sixth Day of July, 2004

JON W. DUDAS
*Acting Director of the United States Patent and Trademark Office*